United States Patent [19]

Kloek

[11] 4,139,700
[45] Feb. 13, 1979

[54] PROCESS FOR THE PREPARATION OF BICYCLOTHIADIAZINONES

[75] Inventor: James A. Kloek, Overland, Mo.

[73] Assignee: Monsanto Company, St. Louis, Mo.

[21] Appl. No.: 819,636

[22] Filed: Jul. 27, 1977

[51] Int. Cl.$^2$ .................. C07D 285/16; C07D 513/04
[52] U.S. Cl. .......................................... 544/10; 544/11
[58] Field of Search .................................... 544/10, 11

[56] References Cited

U.S. PATENT DOCUMENTS

| 3,041,336 | 6/1962 | Teufel | 544/11 |
|---|---|---|---|
| 3,822,257 | 7/1974 | Hamprecht et al. | 544/11 |
| 3,920,641 | 11/1975 | McKendry | 544/10 |
| 4,054,440 | 10/1977 | McKendry | 544/11 |

Primary Examiner—John M. Ford
Attorney, Agent, or Firm—William I. Andress; Donald W. Peterson

[57] ABSTRACT

The disclosure herein relates to a novel process for the preparation of bicyclothiadiazinones. In particular the process involves an acid-catalyzed cyclization of the appropriate sulfamoyl acid or ester using a mixture of trifluoroacetic acid and trifluoroacetic anhydride as catalyst.

11 Claims, No Drawings

PROCESS FOR THE PREPARATION OF BICYCLOTHIADIAZINONES

BACKGROUND OF THE INVENTION

1. Field of the Invention

The invention herein pertains to the field of bicyclothiadiazinones and processes for their preparation.

2. Description of the Prior Art

Thiadiazinone dioxides as a class are known compounds. Unsubstituted or substituted benzo- and pyridothiadiazinone dioxides have been disclosed in the art.

Exemplary processes for preparing the above compounds include cyclizing the corresponding o-sulfamidobenzoic acids in the presence of phosgene and a basic catalyst (U.S. Pat. No. 3,822,257) or cyclizing the corresponding pyridinecarboxylate with a condensing agent such as phosphorus oxychloride, thionyl chloride or aqueous or alcoholic alkaline solutions, e.g., methanol, sodium methylate, aqueous sodium hydroxide or the like (U.S. Pat. Nos. 3,920,641 and 3,989,507). The same condensing agents have also been used to cyclize N-alkyl-N'-o-carboxyphenyl sulfamides or N-alkyl-N'-o-carboalkoxyphenyl sulfamides (U.S. Pat. No. 3,708,277) or other sulphaamido carboxylic acid derivatives (U.S. Pat. No. 3,940.389).

Still another method of preparing certain of the above compounds is to cyclize the corresponding N-acyl sulphamides in the presence of acid-binding agents such as alkali carbonates or alcoholates or tertiary organic bases (U.S. Pat. No. 3,041,336).

It has been found that in some cases cyclizations proceed in poor yields in basic media when bulky substituents, e.g., branched chain alkyl groups, are present on the N' atom of the intermediate sulphamido compound.

Accordingly, it is an object of this invention to provide a process for preparing the title compounds which proceeds smoothly without regard to the nature of the N' substituent, i.e., whether in the case of alkyl substituents they are linear or branched chain in configuration.

SUMMARY OF THE INVENTION

The present invention relates to a novel process for the preparation of bicyclothiadiazinone dioxides, members of which have biological activity as plant growth regulators, e.g., as heat or cold stress relief agents or as plant morphology modifiers or herbicides, e.g., as post-emergence herbicides.

In more particular, the present invention relates to a process for preparing compounds of the formula

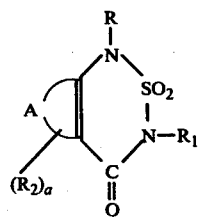

wherein

R, $R_1$ and $(R_2)_a$ independently represent hydrogen, alkyl, alkenyl, alkynyl, alkoxy, alkoxyalkyl, polyalkoxy, cycloalkyl, aryl, aralkyl, alkarylene, acyl, alkoxycarboalkyl or analogs thereof substituted with halo, nitro, hydroxy, cyano, $CF_3$, alkylthio or mono-or dialkylamino or alkanolamino groups;

A comprises an alkylene group having up to 6 carbon atoms or the residue of a phenylene radical or a heterocyclic ring having up to 7 ring atoms at least one of which is O, $S(O)_x$, $P(O)_y R_3$ or $N(R_3)_z$, where $R_3$ is the same as $R-R_2$;

a is 0–4, x is 0, 1 or 2 and y and z are 0 or 1 which comprises reacting a sulfamoyl acid or ester of the formula

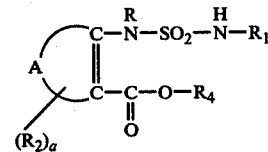

where A, R, $R_1$, $R_2$ and a have the meanings given above and $R_4$ is hydrogen or t-butyl, with an acid catalyst comprising a mixture of trifluoroacetic acid and the trifluoroacetic anhydride under conditions sufficient to cyclize said ester. While ratios of said acid to said anhydride may range from about 9:1 to 1:9, a preferred ratio is about 1:1. This process may suitably be conducted at a temperature within the range of about −78° to 150° C. and preferably within the range of about 0° to 100° C. at subatmospheric, atmospheric or superatmospheric pressures for a period within the range of about 0.1 to 72 hours, although some cyclizations occur instantaneously.

In one aspect of this invention, a novel process has been found for the preparation of the sulfamoyl esters which are cyclized to the final product.

It is known how to prepare sulfamoyl esters by the reaction of certain heteroaromatic enamino esters with sulfamoyl chloride in the presence of a base, e.g. triethylamine. However, in applicant's experience, the reaction of alkyl-2-aminocyclohexenecarboxylates with sulfamoyl chloride in the presence of triethylamine has led to reduced yields of the desired sulfamoyl ester due to co-production of products substituted on the α-carbon of the enamino ester which then react to form other by-products. Such process is illustrated in Example 1.

DESCRIPTION OF PREFERRED EMBODIMENTS

EXAMPLE 1

A solution of 8.45 g (0.05 mol) of 2-aminocyclohexene carboxylic acid, ethyl ester and 10.1 g (0.1 mol) of triethylamine (TEA) in benzene was cooled to 10° C. and a solution of 8.7 g (0.055 mol) of N-isopropyl sulfamoyl chloride was added dropwise. The resulting solution was washed with water, dried, filtered and concentrated. The residue was treated with 20% ethylacetate/80% cyclohexane on dry column silica gel, and the isolated fraction recrystallized from cyclohexane in 16% yield. The product was identified by NMR and elemental analysis as 2-(isopropyl sulfamido)-1-cyclohexene-1-carboxylic acid, ethyl ester.

| anal.: Calc'd for $C_{12}H_{22}N_2O_4S_1$ | Calc'd | Found |
|---|---|---|
| C | 49.63 | 49.36 |
| H | 7.64 | 7.76 |

| anal.: Calc'd for $C_{12}H_{22}N_2O_4S_1$ | Calc'd | Found |
|---|---|---|
| N | 9.65 | 9.50 |

EXAMPLE 2

Applicant believed that further suppression of unwanted by-products could be achieved. In the presence of TEA, this reaction is complete in less than five minutes at 5° C. The TEA removes HCl from the sulfamoyl chloride to form a highly reactive intermediate referred to as an azosulfene or sulfonyl amine. This species is so reactive that it demonstrates very little selectivity.

It was reasoned that a base much weaker than TEA as an HCl scavenger would be expected to help in one of two ways. First, if the base were sufficiently weak, azo sulfene formation would be completely suppressed, thus forcing the reaction to proceed by direct chloride displacement by the enamino ester. Alternatively, the weak base could very slowly generate azo sulfene, and thus keep its concentration in solution at all times very low. Both of these effects would be expected to improve selectivity. The logical choice for such a base seemed to be a second equivalent of the enamino ester itself. Gratifyingly, reaction of two equivalents of the above ethyl ester in Example 1 with one equivalent of N-isopropyl sulfamoyl chloride completely eliminated the formation of α-carbon substituted material. There was a corresponding 10% increase in the yield of N-substituted material.

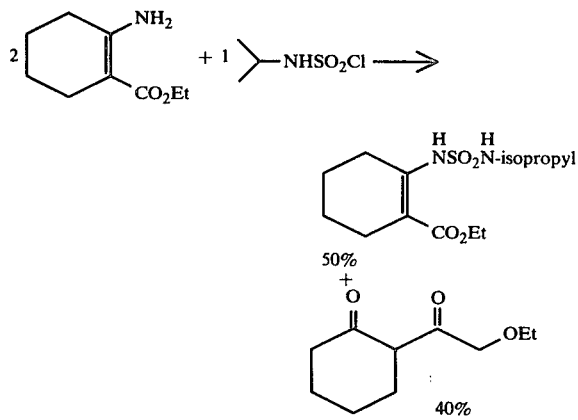

Since a large amount of starting material was recovered, it was believed that the purity of the sulfamoyl chloride was responsible for lower than expected yields. Accordingly, fresh sulfamoyl chloride was prepared of high purity. A sample of high purity N-ethylsulfamoyl chloride was reacted with the above ethyl ester of Example 1 under the conditions above. A high yield of a product, presumably the one shown, was obtained. Fortunately, this compound spontaneously cyclized in the work-up to afford the desired tetrahydrobenzothiadiazinone in an overall yield of greater than 75%.

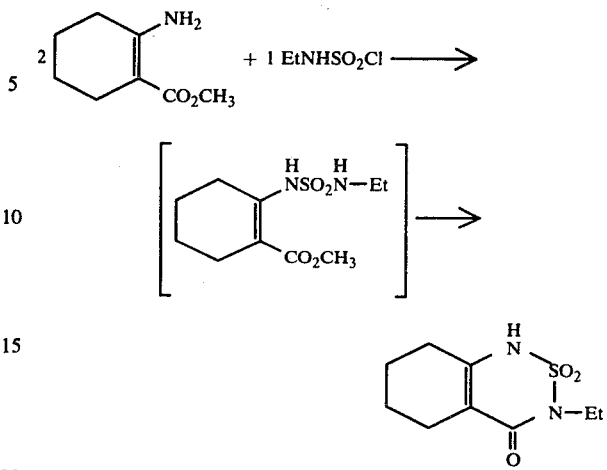

A procedure is therefore now in hand which provides for the condensation of β-enamino esters with sulfamoyl chlorides in high yield and with excellent resiospecificity. This is an excellent first step for a general, two-step synthesis of tetrahydrobenzothiadiazinones.

EXAMPLE 3

This example illustrates the preparation of a precursor sulfamoyl ester of this invention, i.e., 2-(isopropyl sulfamido)-1-cyclohexene-1-carboxylic acid, t-butyl ester.

A solution of 2 equivalents of t-butyl-2-amino-1-cyclohexene carboxylate in benzene was cooled to 5° and treated with 1 equivalent of N-isopropyl sulfamoyl chloride. The resulting solution was stirred 48 hours at room temperature, washed with water, dried over $MgSO_4$ and concentrated to produce the compound in the lead paragraph of this example in 73% yield; m.p. 97–99° C. (from pentane).

| Anal.: Calc'd for $C_{14}H_{26}N_2O_4S_1$ | Calc'd | Found |
|---|---|---|
| C | 52.80 | 52.68 |
| H | 8.23 | 8.28 |
| N | 8.80 | 8.71 |

The β-enamino esters used as starting materials in the process of this invention are readily prepared, e.g., as follows:

Two equivalents of sodium metal are dissolved in a convenient amount of an appropriate alcohol, e.g., methanol, ethanol or butanol. To this solution is added 1 equivalent of cyclohexene carbamate and the resulting mixture refluxed for 18 hours. After cooling, the solution is poured into twice its volume of water and extracted with ether. The extract is washed with brine, dried over $MgSO_4$ and concentrated, e.g., on a rotary evaporator.

EXAMPLE 4

This example describes the preparation of 3-isopropyl-5,6,7,8-tetrahydro-2,1,3-benzothiadiazin-4-(3H)one-2,2-dioxide by the acid-catalyzed ring closure of the precursor sulfamoyl esters prepared in accordance with the process described in Example 1.

A solution of 0.75 g of 2-(isopropyl sulfamido)-1-cyclohexene-1-carboxylic acid, t-butyl ester in 5 ml. of trifluoroacetic acid and 5 ml. of trifluoroacetic anhydride was stirred at room temperature for 5 minutes. The solvents were evaporated and the resulting solid triturated with hexane to provide 0.5 g (87%) of the cyclic sulfamide named in the preceding paragraph; m.p. 188–192°.

| Anal. Calc'd. for $C_{10}H_{16}N_2O_3S_1$ | | Calc'd. | Found |
|---|---|---|---|
| | C | 49.16 | 49.19 |
| | H | 6.60 | 6.60 |
| | N | 11.47 | 11.42 |

EXAMPLE 5

This example illustrates the preparation of 1H-2,1,3-benzothiadiazin-4(3H)-one, 3-cyclohexyl,5,6,7,8-tetrahydro,2,2-dioxide.

One equivalent of cyclohexyl sulfamoyl chloride was added to two equivalents of 2-aminocyclohexene carboxylic acid, t-butyl ester in benzene. After stirring at room temperature for 2 days, the solution was washed with water, dried, filtered and stripped. The residue gave a crystalline product from pentane; yield 35%, m.p. 100–102°.

| Anal. Calc'd. for $C_{17}H_{30}N_2O_4S$ | | Calc'd. | Found |
|---|---|---|---|
| | C | 56.95 | 56.68 |
| | H | 8.43 | 8.45 |
| | N | 7.81 | 7.76 |

The product was thus identified as 1-cyclohexene-1-carboxylic acid, t-butyl ester, [2(cyclohexylsulfamoylamino)]. Two grams of this product were dissolved in 20 ml. of a 50/50 mixture of trifluoroacetic acid/trifluoroacetic anhydride. This solution was stirred at room temperature for 1 hour. The crystallized product was filtered from the reaction mixture, recovered in 79% yield; m.p. 208–209° and identified as the compound named in the first paragraph of this example.

| Anal. Calc'd. for $C_{13}H_{20}N_2O_3S$ | | Calc'd. | Found |
|---|---|---|---|
| | C | 54.91 | 54.78 |
| | H | 7.09 | 7.17 |
| | N | 9.85 | 9.76 |

EXAMPLE 6

The same procedure described in Example 5 was followed, except that t-butyl-2-[(N'-n-butyl sulfamoyl)amino]-3-indole carboxylate was prepared and used as the precursor sulfamoyl ester.

The product obtained according to this example was recovered in 26% yield, m.p. 179–181° and identified as 1H,9H-[1,2,6-thiadiazin-(3,4-d)indol-4(3H)-one,3-butyl,2,2-dioxide].

| Anal. Calc'd. for $C_{13}H_{15}N_3O_3S$ | | Calc'd. | Found |
|---|---|---|---|
| | C | 53.18 | 52.94 |
| | H | 5.11 | 5.19 |
| | N | 14.22 | 14.28 |

EXAMPLE 7

To an ice cold solution of 5.0 g (3.18 mmol) of methyl-3-amino-2-thiophene carboxylate and 3.2 g (3.2 mmol) of triethylamine in 120 ml of benzene was added 5.02 g (3.2 mmol) of isopropyl sulfamoyl chloride. The solution was stirred overnight, washed with water, dried, and concentrated to an oil (methyl-3-amino(isopropylsulfamido)-2-thiophene carboxylate). This oil was dissolved in 150 ml of a solution of 17 g of potassium hydroxide in 200 ml of ethanol and refluxed 1 hour. After pouring over ice (ca. ~400 ml total soln) the mixture was acidified with concentrated hydrochloric acid, and extracted three times with ethyl acetate. Drying and concentration afforded a solid (i.e., the acid corresponding to the above ester) which was dissolved in a solution of 40 ml of triflouroacetic anhydride and 20 ml of trifluoroacetic acid. After stirring 0.5 hr., the solvent was pumped off, and the product was recrystallized from benzene and recovered in 57% yield; m.p. 138–140°

| Anal. Calc'd. for $C_8H_{10}N_2O_3S_2$ | | Calc'd. | Found |
|---|---|---|---|
| | C | 38.01 | 38.82 |
| | H | 4.09 | 4.15 |
| | N | 11.37 | 11.38 |

The final product was identified as 1H-thieno[3,2-d]-1,2,6-thiadiazin-4(3H)-one-3-isopropyl,2,2dioxide.

EXAMPLE 8

Following the same procedure described in Example 5, but substituting pyrazole-4-carboxylic acid, ethyl ester, 5-ethyl sulfamoyl amino as the precursor sulfamoyl ester, the corresponding carboxylic acid is produced and after treatment with the acid catalyst, 2H-pyrazole[3,4-e]-2,1,3-thiadiazin-4-(3H)-one-3-isopropyl,2,2-dioxide is obtained.

EXAMPLE 9

Using a 50/50 mixture of trifluoroacetic acid/trifluoroacetic anhydride as cyclizing agent, the product 1H-2,1,3 Benzo - thiadiazin-4(3H)-one-3-isopropyl,2,2-dioxide is prepared from the corresponding sulfamoyl ester.

This procedure has distinct advantages over prior art procedures using methanolic sodium hydroxide or phosgene as condensing agents in that yields are not reduced when the alkyl substituent on the N-3 nitrogen in the above structural formula is a branched chain radical, e.g., isopropyl or t-butyl. In addition, when the sulfamoyl acid is cyclized with phosgene to prepare the above product, the free acid is difficult to work with in some cases, impossible to prepare in others.

In the present process, use of sulfamoyl esters gives rise to the corresponding acid in situ, which then cyclizes in high yield. Depending upon the physical characteristics and properties of the starting materials and products the precursor sulfamoyl esters may be prepared by reacting the starting materials, viz., the 2-aminocyclohexenecarboxylate and sulfamoyl chlorides at temperatures generally within the range of about 31 78° C. to 150° C. and preferably from about 0° C. to 35° C., at subatmospheric, atmospheric or superatmospheric pressures and reaction times of from about 1 to 72 hours. The thus-prepared sulfamoyl esters are then subjected to ring closures at temperatures within the general range of about −78° C. to 150° C. and preferably from about 0° C. to 100° C. at subatmospheric, atmospheric or superatmospheric pressures and times within the range of from about 0.1 to 72 hours; although some of these cyclizations occur instantaneously.

The final product may be recovered by conventional techniques such as distillation, recrystallization, etc. Suitable solvents herein include alcohols, alkanes, halogenated alkanes, cycloalkanes, esters of lower aliphatic alcohols and acids, aromatic hydrocarbons or mixtures thereof. Exemplary solvents include aqueous ethanol, pentane, cyclohexane, methylcyclohexane, chloroform, ethyl acetate, toluene, the xylenes, ether/pentane, ethanol/nitromethane, etc.

Products within the above generic formula which are preparable according to the process of this invention include those wherein the indicated R, $R_1$ to $R_2$ groups have up to 12 carbon atoms and preferably up to 6 carbon atoms. Further exemplary products include the novel compounds disclosed and claimed in applicant's copending application Ser. No. 819,635 filed July 27, 1977, wherein A in the above structural formula is the residue of carbocylic ring having up to 6 carbon atoms or a heterocyclic residue having up to 7 ring atoms. Compounds of preferred interest which may be prepared according to the process of this invention include 5,6,7,8-tetrahydro-3-isopropyl-benzo (1H)-2,1,3-thiadiazin-4-one-2,2-dioxide, 1H-pyrido[3,4-e]-2,1,3-thiadiazin-4(3H)-one,5,6,7,8-tetrahydro, 3-ethyl, 6-acetyl, 2,2-dioxide, 1H-thieno-[3,2-d]-1,2,6-thiadiazin-4(3H)-one, 3-n-butyl, 2,2-dioxide, 1H-pyrido[2,3-e]2,1,3-thiadiazin-4(3H)-one, 3-isopropyl, 2,2-dioxide, 1H-3-isopropyl-2,1,3-Benzothiadiazin-4(3H)-one,2,2-dioxide.

Among the compounds prepared according to the process of this invention are those having utility as herbicides, plant growth regulators and pharmaceuticals, e.g., antiphlogistics, antipyretics, analgetics and psycholeptics. See, e.g., U.S. Pat. Nos. 3,041,336, 3,217,001, 3,708,277, 3,940,389, 3,920,641 and 3,989,507.

While the illustrative embodiments of the invention have been described in detail, it will be understood by those skilled in the art that modifications can be made without departing from the spirit and scope of the appended claims.

I claim:

1. Process for preparing a compound of the formula

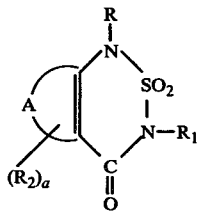

wherein

R, $R_1$ and $(R_2)_a$ independently represent hydrogen, alkyl, alkenyl, alkynyl, alkoxy, alkoxyalkyl, polyalkoxy, cycloalkyl, aromatic hydrocarbon, lower alkanoyl, alkoxycarboalkyl or analogs thereof substituted with halo, nitro, hydroxy, cyano, $CF_3$, alkylthio or mono- or dialkylamino or alkanolamino groups;

A comprises an alkylene group having up to 6 carbon atoms or the residue of a phenylene radical or a heterocyclic residue having up to 7 ring atoms including O, $S(O)_x$, $P(O)_yR_3$ or $N(R_3)z$ hetero moieties, where $R_3$ is the same as $R-R_2$, the carbon-containing members of which contain up to 12 carbon atoms;

a is 0–4;

x is 0, 1 or 2 and y and z are 0 or 1;

which comprises reacting a sulfamoyl acid or ester of the formula

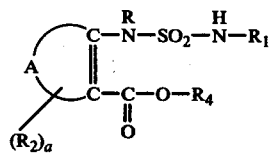

wherein A, R, $R_1$, $R_2$ and a have the meanings given above and $R_4$ is hydrogen or t-butyl, with an acid catalyst comprising a mixture of trifluoroacetic acid and trifluoroacetic anhydride at temperatures within the range of −78 to 150° C. to cyclize said ester.

2. Process according to claim 1 wherein A is an alkylene chain, R is hydrogen and $R_1$ is alkyl.

3. Process according to claim 2 wherein said compound is 5,6,7,8-tetrahydro-3-isopropyl-benzo (1H)-2,1,3-thiadiazin-4-one-2,2-dioxide.

4. Process according to claim 1 wherein A is a heterocyclyl residue, R is hydrogen and $R_1$ is alkyl.

5. Process according to claim 4 wherein the hetero atom is nitrogen.

6. Process according to claim 5 wherein said compound is 1H-pyrido-[3,4-e]-2,1,3-thiadiazin-4(3H)-one,5,6,7,8-tetrahydro, 3-ethyl, 6-acetyl, 2,2-dioxide.

7. Process according to claim 4 wherein the hetero atom is sulfur.

8. Process according to claim 7 wherein said compound is 1H-thieno-[3,2-d]-1,2,6-thiadiazin-4(3H)-one,3-n-butyl,2,2-dioxide.

9. Process according to claim 1 wherein A is the residue of a phenylene radical, R and $R_1$ are hydrogen or alkyl.

10. Process according to claim 9 wherein said compound is 1H-pyrido[2,3-e]-2,1,3-thiadiazin-4(3H)-one-3-isopropyl,2,2-dioxide.

11. Process according to claim 1 wherein said sulfamoyl esters are prepared by reacting two equivalents of the appropriate enamino ester with one equivalent of the appropriate sulfamoyl halide.

* * * * *